United States Patent [19]

Sugier et al.

[11] 4,126,581

[45] Nov. 21, 1978

[54] CATALYST CONTAINING COPPER OXIDE AND ZINC OXIDE, ITS MANUFACTURE AND ITS USE FOR THE CONVERSION OF CARBON MONOXIDE

[75] Inventors: André Sugier, Rueil Malmaison; Philippe Courty, Houilles; Edouard Freund, Rueil Malmaison, all of France

[73] Assignee: Societe Francaise des Produits pour Catalyse, France

[21] Appl. No.: 801,261

[22] Filed: May 27, 1977

[30] Foreign Application Priority Data

May 28, 1976 [FR] France .................................. 76 16432

[51] Int. Cl.$^2$ .......................... B01J 21/04; B01J 23/06
[52] U.S. Cl. ..................................... 252/463; 252/475; 260/449.5; 423/656
[58] Field of Search ....................... 252/463, 475, 476; 423/656; 260/449.5

[56] References Cited

U.S. PATENT DOCUMENTS

| | | | |
|---|---|---|---|
| 3,388,972 | 6/1968 | Reitmeier et al. | 252/463 X |
| 3,546,140 | 12/1970 | Gutmann et al. | 423/656 X |
| 3,663,457 | 5/1972 | Tamura et al. | 252/463 |
| 3,922,337 | 11/1975 | Campbell et al. | 423/656 |
| 3,961,037 | 6/1976 | Davies et al. | 423/656 |
| 3,969,542 | 7/1976 | Tomita et al. | 252/463 X |

*Primary Examiner*—Edward J. Meros
*Attorney, Agent, or Firm*—Millen & White

[57] ABSTRACT

Catalyst for the conversion of carbon monoxide in the presence of water, to produce hydrogen, or in the presence of hydrogen, to produce methanol, said catalyst containing 10 – 60% by weight of copper oxide, 5 – 40% by weight of zinc oxide and 30 – 70% by weight of aluminous cement, the total content of copper oxide and zinc oxide being from 30 to 70% by weight.

12 Claims, No Drawings

CATALYST CONTAINING COPPER OXIDE AND ZINC OXIDE, ITS MANUFACTURE AND ITS USE FOR THE CONVERSION OF CARBON MONOXIDE

Catalysts for the conversion of carbon monoxide and methanol synthesis, based on copper oxides and zinc oxides, have already been described (Larson, U.S. Pat. No. 1 797 426) and have been further improved in order to increase their efficiency and life time.

It has been discovered that the activity and particularly the stability of the catalysts based on copper oxide and zinc oxide were significantly increased by the manufacturing process and the stabilizing agent used according to the invention.

The constituting elements, copper oxide and zinc oxide or their precursors are admixed with an aluminous cement used in specific proportions and water is added to obtain the hardening of the mixture. Shaping, for example into pellets or pills, may be performed before or after water addition. The final step is usually a calcination, for example at 200°–600° C.

Copper oxide and zinc oxide may be used either as oxides, for example CuO and ZnO, or in the form of other compounds, for example salts. According to a preferred technique, there is used, as precursors of ZnO and CuO, thermally decomposable salts, such as nitrates, formates, acetates or carbonates. This decomposition is obtained by heating at a temperature of, for example, 200° to 600° C., performed for example during the above-mentioned calcination.

The content by weight of copper oxide, expressed as CuO, is preferably from 10 to 60% and the content by weight of ZnO from 5 to 40%, the total content of copper oxide and zinc oxide being from 30 to 70% by weight; the content of aluminous cement is from 30 to 70%. A preferred composition is approximately by weight: 20–30% CuO, 20–30% ZnO and 40–60% aluminous cement. These values are given as dry weight. They correspond to both the final catalyst and the ingredients involved in the preparation. The weight of these ingredients must be such that it correspond to said values calculated as CuO, ZnO and aluminous cement. The weights are calculated in a dry state.

Shaping may be performed in any manner known for making, for example, pellets or, preferably, pills. One of the advantages of making use of a refractory cement is to make possible the shaping into pills of the product even for high contents of active oxides (up to 70% by weight) while ensuring a very good mechanical strength and a very good stabilization of the active phase, i.e. the maintenance of the catalyst activity over long periods.

By aluminous cement, it is meant a cement which contains, by weight, from 10 to 50% of CaO and/or BaO and from 30 to 85% of $Al_2O_3$, the total content of CaO + BaO + $Al_2O_3$ being at least 70% by weight. Other oxides may be present as impurities, for example $SiO_2$, $Fe_2O_3$ and $TiO_2$. The content of each of the latter oxides is preferably lower than 10% by weight.

The main constituents of these cements are $Al_2O_3$, CaO (or $Al_2O_3$, BaO) and 2 $Al_2O_3$, CaO. In the final catalyst, the content of said aluminates is usually from 15 to 40%, preferably from 20 to 30% (analysis by X-ray diffraction).

The use of an aluminous cement is an important feature of the invention. As a matter of fact, it has been observed that the use of a conventional cement such as Portland cement, resulted in catalysts which rapidly lose their initial strength, particularly in the presence of steam.

The final step is a calcination, for example at 200°–600° C., preferably 325°–450° C.; a reduction by means of hydrogen may follow, for example at 100°–400° C. By calcination it is meant heating in the presence of an oxygen-containing gas, for example air.

The setting of the cement may be favoured by adding ammonium carbonate, for example in the form of an aqueous solution; there will be preferably used solutions at 10–100g of ammonium carbonate per liter.

The setting time of the cement is not per se a critical feature, Setting times of 1 hour or more are usually satisfactory.

The reactions of CO and $CO_2$ conversion by hydrogen are essentially as follows:

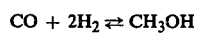

$$CO + 2H_2 \rightleftarrows CH_3OH$$

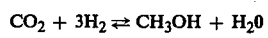

$$CO_2 + 3H_2 \rightleftarrows CH_3OH + H_2O$$

The operating conditions, in the presence of catalysts are well known. It is preferred to proceed under a pressure of from 20 to 200 bars and at a temperature of from 200° to 300° C.

The reaction of carbon monoxide conversion by steam is the following:

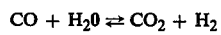

$$CO + H_2O \rightleftarrows CO_2 + H_2$$

The operating conditions are also well known. The operating temperature is preferably from 150° to 350° C., more preferably from 170° to to 250° C.

By way of example, several catalysts have been prepared. Catalysts A, $E_1$ and $E_2$ are reference catalysts, not conform with the invention.

Catalyst A is prepared as follows:

In a crushing mixer 347 g of zinc carbonate having a 72% (b.w.) content of zinc oxide ZnO and 350 g of basic copper carbonate having a 72% content of copper oxide, are admixed with 500 g of alumina having a specific surface of 300 $m^2g^{-1}$.

To the resulting mixture, crushed to grains of a size lower than 2 μ, there is added 3% of graphite and the powder is shaped into pellets of 5 mm height and 5 mm diameter.

The pellets are then maintained for 2 hours at 400° C. in air.

The resulting catalyst has a total pore volume of 31 ml/100 g and its mechanical strength, measured with a LHOMARGI apparatus, is 60 kg/$cm^2$.

CATALYST B

In a crushing mixer, 347 g of zinc carbonate having a 72% by weight content of zinc oxide and 350 g of basic copper carbonate having a 72% by weight content of copper oxide, are admixed with 500 g of aluminous cement (Super Secar Laffarge).

The latter cement, as used, had the following average composition (in percent by weight): $Al_2O_3$ = 81, CaO = 17, $Na_2O$ = 0.8, $SiO_2$ = 0.1, $Fe_2O_3$ = 0.1; the content of each of the other components is lower than 0.1%.

To the intimately mixed powder, whose grain size is lower than 2 microns, there is added 250 ml of water. The resulting product is shaped into pellets of 5 mm height and 5 mm diameter which are allowed to mature for 12 hours in an atmosphere saturated with water at 40° C., and then maintained for 2 hours at 400° C. in air. The analysis, by X-ray diffraction, indicates that the content by weight of the catalyst in calcium aluminates $Al_2O_3$, CaO and 2 $Al_2O_3$, CaO is 23.8%.

The resulting catalyst has a total pore volume of 29 ml/100 g and its mechanical strength, as measured in a LHOMARGI apparatus, is 110 kg/cm².

CATALYST C

In a crushing mixer, 347 g of zinc carbonate with a 72% by weight zinc oxide content and 350 g of copper carbonate with a 72% by weight copper oxide content, are admixed with 500 g of Super Secar Laffarge cement. The resulting powder, whose grain size is lower than 2 microns, is then shaped into balls of 4 to 7 mm of diameter in a revolving pill-shaper while pulverizing 272 ml of water on the powder.

The balls are then matured for 12 hours at 40° C. in atmosphere saturated with water and then maintained for 2 hours at 400° C. in air.

The resulting catalyst has a total pore volume of 30 ml/100 g and its mechanical strength, measured by a LHOMARGI apparatus, is 18 kg F. The analysis, by X-ray diffraction, indicates that the catalyst content in calcium aluminates $Al_2O_3$, CaO and 2 $Al_2CaO$ is 26% by weight.

CATALYST D

A catalyst D having the same composition as that of catalyst C is prepared according to the same technique, except that in the step of pill-shaping there is pulverized 275 ml of a solution containing 40 g/l of ammonium carbonate.

After maturation and activation in the same conditions as for catalyst C, the catalyst D has a pore volume of 32 ml/100 g and its mechanical strength, measured with a LHOMARGI apparatus, is 24 kg F.

The analysis, conducted as precedingly, shows a calcium aluminates content amounting to 26.4%.

CATALYSTS $E_1$ and $E_2$ 347 g of zinc carbonate having a 72% by weight content of zinc oxide and 350 g of basic copper carbonate with a 72% by weight content of copper oxide, are mixed with 150 g of aluminous cement (Super Secar Laffarge) and 350 g of alumina having a specific surface of 300 m² g⁻¹, used as diluent.

The resulting powder, having a grain size lower than 2 μ, is subdivided into two portions.

One of the portions is used for making balls as described for the manufacture of catalyst C; the yield of balls is smaller than 30%. The resulting balls are matured for 12 hours at 40° C. in an atmosphere saturated with water and maintained for 2 hours at 400° C. in air. The resulting catalyst $E_1$ has a mechanical strength, measured with a LHOMARGI apparatus, lower than 0.5 kg F which makes impossible its use in an industrial reactor.

The second portion of the powder, after addition of 80 ml of water, is shaped into pellets of 5 mm height and 5 mm diameter which are matured for 12 hours in an atmosphere saturated with water at 40° C. and then maintained for 2 hours at 400° C. in air.

The resulting catalyst $E_2$ has a total pore volume of 28 ml/100 g and its mechanical strength, measured in LHOMARGI apparatus is 110 kg/cm².

The catalytic activity is then measured for the conversion of carbon monoxide by water and by hydrogen with the use of the so-prepared different catalysts. This measurement is conducted after activation of the catalyst under atmospheric pressure at 180° C., by passing a gas consisting of 1% by volume and 99% of nitrogen for 48 hours with a VVH of 500 (VVH = Gas volume/volume of catalyst/hour).

EXAMPLE 1

The activity of the so-prepared catalyst for the conversion of carbon monoxide, by means of water, to $CO_2$ and $H_2$ has been measured in the following manner:

Over 100 ml of a catalyst placed in a cylindrical reactor of a 30 mm diameter, maintained at a temperature of 195° C., there is passed a gas having the following composition: (% by volume)

$$CO = 4, CO_2 = 23, H_2 = 70, CH_4 + N_2 = 3$$

and steam (ratio of steam to the input gas = 0.8) at a VVH (volume of dry gas per volume of catalyst and per hour) of 8500, under a pressure of 20 bars. At the outlet of the reactor the issuing gases are analyzed and the percentage of carbon monoxide converted to $CO_2$ and $H_2$ is deduced therefrom:

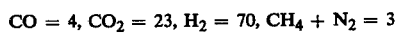

(CO moles at the inlet − CO moles at the outlet /CO moles at the inlet)

The following results have been obtained

| CATALYST | HOURS OF RUN | CONVERTED CO % |
|---|---|---|
| A | 1 | 93 |
|   | 10 | 92 |
|   | 100 | 87 |
| B | 1 | 94 |
|   | 10 | 92 |
|   | 100 | 90 |
| C | 1 | 95 |
|   | 10 | 93 |
|   | 100 | 92 |
| D | 1 | 96 |
|   | 10 | 94 |
|   | 100 | 93 |
| $E_2$ | 1 | 94 |
|   | 100 | 88 |

The conversion of CO and $H_2O$ to $H_2$ is more than 99% selective.

After 100 hours of test, the mechanical strength of the catalyst is measured with a LHOMARGI apparatus. The following results have been obtained:

| CATALYST | MECHANICAL STRENGTH |
|---|---|
| A | 35 kg/cm² |
| B | 78 kg/cm² |
| C | 15 kg F |
| D | 22 kg F |
| $E_2$ | 65 kg/cm² |

EXAMPLE 2

The activity of the catalyst for the conversion with hydrogen of carbon monoxide to methanol is measured by passing over 100 ml of catalyst, under a pressure of 100 bars at 250° C. and with a VVH (volume of gas at normal temperature and pressure per volume of catalyst and per hour), a gas having the following composition (% by volume):

$$CO = 4.5, CO_2 = 4, H_2 = 84, N_2 = 7.5$$

At the outlet of the reactor, the formed products are analyzed and the rate of conversion expressed as mole of methanol per mole of CO and $CO_2$ at the inlet of the reactor, is deduced therefrom.

The main results are reported in the following table; they concern respectively the initial activity of the catalyst i.e. after 48 hours of operation ($t = 48$) and the activity after 200 hours of operation ($t = 200$)

| CATALYST | CONVERSION of CO to CH$_3$OH | | CONVERSION of CO$_2$ to CH$_3$OH | |
|---|---|---|---|---|
| | t = 48 h | t = 200 h | t = 48 | t = 200 |
| A | 51.3 | 44.1 | 41.5 | 34.4 |
| B | 52.4 | 50.3 | 43.0 | 40.7 |
| C | 52.9 | 51.0 | 43.1 | 41.7 |
| D | 53.6 | 52.1 | 43.3 | 41.9 |
| E$_2$ | 51.4 | 47.0 | | |

EXAMPLE 3

Another advantage of the use of an aluminous cement for the manufacture of the catalyst lies in the obtainment of catalysts which are more resistant to poisoning by sulfur and which are regenerable.

As a matter of fact, when the charge contains sulfur compounds, it is observed that catalysts containing an aluminous cement are not only more resistant but may be regenerated by calcination, either in the presence of air or in the presence of steam or in the presence of a mixture of said two compounds with an inert gas acting as diluent, such for example as nitrogen.

The capacity of these catalysts to be regenerated is shown by the following tests:

Example 1 is repeated except that 500 parts of H$_2$S per million of parts by volume are added to the gaseous charge and the treatment is discontinued when the sulfur content of the catalyst amounts to 5% by weight; the activity of the catalyst for the conversion of carbon monoxide, as above described, is then measured. The catalyst is then subjected to a limited oxidation by scavenging at 200° C. with 0.5% of oxygen in nitrogen. At the end of this step, heating at 400° C. is conducted for 4 hours in air and then the catalyst is reduced at 200° C. with 1% hydrogen in nitrogen and finally an activity test is performed.

The following results have been obtained:

| | CONVERTED CO% | |
|---|---|---|
| | BEFORE REGENERATION | AFTER REGENERATION |
| A | 12 | 22 |
| B | 28 | 89 |
| C | 30 | 90 |
| D | 31 | 90 |
| E$_2$ | 15 | 43 |

The production of H$_2$ is more than 99% selective.

What we claim is:

1. A catalyst containing 10–60% by weight of copper oxide, 5–40% by weight of zinc oxide and 30 to 70% of aluminous cement, the total content of copper oxide and zinc oxide being from 30 to 70% by weight, said aluminous cement containing 10–50% by weight of CaO and from 30 to 85% by weight Al$_2$O$_3$, the total content of CaO and Al$_2$O$_3$ being at least 70% by weight and being sufficient to provide at least 15–50% of calcium aluminates based on the weight of the catalyst.

2. A catalyst according to claim 1, which contains 20–30% of copper oxide, 20–30% of zinc oxide and 40–60% of said aluminous cement.

3. A process for manufacturing a catalyst according to claim 1 comprising admixing an aluminous cement with a copper compound and a zinc compound, in proportions calculated as CuO, ZnO and said aluminous cement, respectively of 10–60%, 5–40% and 30–70% of dry weight, adding water to the mixture, shaping the latter and heating to convert the zinc and copper compounds to the corresponding oxides and to activate the catalyst.

4. A process according to claim 3, in which the mixture is shaped before hardening of the cement.

5. A process according to claim 4, in which the mixture is shaped to pills.

6. A process according to claim 3 wherein ammonium carbonate is added to the mixture of the copper compound and the zinc compound.

7. A process according to claim 3, wherein the copper and zinc compounds are copper and zinc salts which are decomposable by heating to the corresponding oxides at a temperature of from 200° and 600° C.

8. A process according to claim 3, wherein the copper and zinc compounds are respectively zinc carbonate and copper carbonate.

9. A process according to claim 3, wherein said heating is carried out at 200°–600° C. in the presence of a molecular oxygen-containing gas.

10. A catalyst produced by the process of claim 9.

11. A catalyst in the form of pills produced by the process of claim 5.

12. A catalyst according to claim 1, containing 20–30% by weight of said calcium aluminates.

* * * * *

UNITED STATES PATENT AND TRADEMARK OFFICE
CERTIFICATE OF CORRECTION

PATENT NO. : 4,126,581
DATED : November 21, 1978
INVENTOR(S) : ANDRE SUGIER ET AL It is certified that error appears in the above-identified patent and that said Letters Patent are hereby corrected as shown below:

Claim 1, line 20: reads "least 15-50% of"
should read -- least 15-40% of --
Claim 3, line 25: reads "admixing an"
should read -- admixing said --

Signed and Sealed this

Twentieth Day of February 1979

[SEAL]

Attest:

RUTH C. MASON
Attesting Officer

DONALD W. BANNER
Commissioner of Patents and Trademarks